United States Patent [19]

Lorenz

[11] Patent Number: 4,550,126

[45] Date of Patent: Oct. 29, 1985

[54] HYDROPHILIC, FLEXIBLE, OPEN CELL POLYURETHANE-POLY(N-VINYL LACTAM) INTERPOLYMER FOAM AND DENTAL AND BIOMEDICAL PRODUCTS FABRICATED THEREFROM

[75] Inventor: Donald H. Lorenz, Basking Ridge, N.J.

[73] Assignee: Hydromer, Inc., Whitehouse, N.J.

[21] Appl. No.: 694,926

[22] Filed: Jan. 25, 1985

[51] Int. Cl.$^4$ .............................................. C08G 18/14
[52] U.S. Cl. ..................... 521/159; 521/137
[58] Field of Search ................................ 521/137, 159

[56] References Cited

U.S. PATENT DOCUMENTS

| | | | |
|---|---|---|---|
| 2,726,219 | 12/1955 | Hill | 521/76 |
| 2,901,445 | 8/1959 | Harris | 521/76 |
| 2,965,584 | 12/1960 | Elkin | 521/128 |
| 3,270,032 | 8/1966 | Erner | 521/115 |
| 3,383,351 | 5/1968 | Stamberger | 521/137 |
| 3,694,301 | 9/1972 | Gruenewald et al. | 521/76 |
| 3,746,663 | 7/1973 | Beale et al. | 521/137 |
| 3,890,254 | 6/1975 | Guthrie | 521/76 |
| 3,903,232 | 9/1975 | Wood et al. | 264/157 |
| 3,914,188 | 10/1975 | Carroll et al. | 521/137 |
| 3,961,629 | 6/1976 | Richter et al. | 128/296 |
| 3,972,328 | 8/1976 | Chen | 128/165 |
| 3,975,350 | 8/1976 | Hudgin et al. | 128/165 |
| 3,975,567 | 8/1976 | Lock | 428/315 |
| 3,978,266 | 8/1976 | Lock | 128/156 |
| 3,978,855 | 9/1976 | McRae et al. | 128/156 |
| 4,100,309 | 7/1978 | Micklus et al. | 428/425 |
| 4,119,094 | 10/1978 | Micklus et al. | 128/132 R |
| 4,127,124 | 11/1978 | Clagett et al. | 128/156 |
| 4,137,200 | 1/1979 | Wood et al. | 521/159 |
| 4,160,076 | 7/1979 | Guthrie et al. | 521/159 |
| 4,202,880 | 5/1980 | Fildes et al. | 424/78 |
| 4,235,988 | 11/1980 | Fildes et al. | 528/79 |
| 4,339,550 | 7/1982 | Palinczar et al. | 521/99 |

*Primary Examiner*—Maurice J. Welsh
*Attorney, Agent, or Firm*—Hoffmann, Dilworth, Barrese & Baron

[57] ABSTRACT

A hydrophilic, flexible, open cell polyurethane-poly(N-vinyl lactam) interpolymer foam is obtained from the process which comprises reacting under interpolymer and foam-forming conditions (a) a substantially linear isocyanate-capped polyether polyol prepolymer having an average reactive functionality of less that about 2.0 with (b) a poly(N-vinyl lactam) and (c) a foam-forming amount of water in the presence of (d) a cell formation-regulating amount of surface active agent. The foams exhibit unexpectedly higher levels of absorptivity for aqueous fluids compared to those of known crosslinked foams. The foams herein are especially useful for the manufacture of a variety of dental and biomedical products including surgical bandages and dressings, laparotomy sponges, medicament carriers, and the like, where the capability for absorbing body fluids is an important performance criterion.

25 Claims, No Drawings

HYDROPHILIC, FLEXIBLE, OPEN CELL POLYURETHANE-POLY(N-VINYL LACTAM) INTERPOLYMER FOAM AND DENTAL AND BIOMEDICAL PRODUCTS FABRICATED THEREFROM

BACKGROUND OF THE INVENTION

This invention relates to cellular polyurethane products and, more particularly, to hydrophilic, flexible, open cell polyurethane-poly(n-vinyl lactam) interpolymer foams and various dental and biomedical products, e.g., laparotomy sponges, bandages and medicament carriers and the like, fabricated therefrom.

U.S. Pat. Nos. 2,726,219, 2,901,445, 3,694,301, 3,890,254, 3,903,232, 4,127,516, 4,137,200 and 4,160,076, among others, show that it is old to prepare a hydrophilic polyurethane foam employing a one-shot or, more commonly, a prepolymer, procedure using water as blowing agent. Each of these prior patents describes the preparation of polyurethane polymers and prepolymers based on polyalkylene ether glycols and organic diisocyanates. Several of the disclosures further describe the use of surface active agents to provide foams having improved cell structure.

U.S. Pat. No. 2,965,584 discloses the preparation of a foamed hydrophilic polyurethane employing a pyrrolidone such as vinylpyrrolidone as catalyst. There is no hint whatever in this patent of forming a foamed polyurethane-polyvinylpyrrolidone interpolymer. While U.S. Pat. Nos. 4,100,309 and 4,119,094 disclose solid polyurethane-polyvinylpyrrolidone interpolymers, there is no suggestion in these patents of preparing foams from such interpolymers.

As shown in U.S. Pat. Nos. 3,961,629, 3,972,328, 3,975,567, 3,978,266, 3,978,855, 4,127,124, 4,202,880, 4,235,988 and 4,339,550, the use of hydrophilic, flexible, open cell polyurethane foams for a variety of medical and surgical applications, including surgical dressings, drug carriers, and the like, is well known. However, there is no suggestion in these patents of using a foamed polyurethane-poly(N-vinyl lactam) interpolymer for any of the medical/surgical applications disclosed therein.

SUMMARY OF THE INVENTION

In accordance with the present invention, a hydrophilic, flexible, open cell polyurethane-poly(N-vinyl lactam) interpolymer foam is obtained from the process which comprises reacting under interpolymer and foam-forming conditions (a) a substantially linear isocyanate-capped polyether polyol prepolymer having an average reactive functionality of less than about 2.0 with (b) a poly(N-vinyl lactam) and (c) a foam-forming amount of water in the presence of (d) a cell formation-regulating amount of surface active agent.

The term "interpolymer" as used herein is intended to indicate that the polyurethane is complexed with, or chemically bound to, the poly(N-vinyl lactam) although the precise nature of the interrelationship is not clearly known at this time. The term "interpolymer" is also intended to exclude mere mechanical mixtures, blends and alloys of polyurethane and poly(N-vinyl lactam).

The foams of this invention exhibit unexpectedly improved absorptivity for aqueous fluids compared with polyurethane foams of known type making them especially useful for the manufacture of a variety of dental and biomedical products including surgical bandages and dressings, laparotomy sponges, medicament carriers, and the like, where the capability for absorbing body fluids is an important performance criterion.

Contrary to expectation, the foams herein possess tensile strengths in the wet condition which are as good as, if not better than, those of known crosslinked polyurethane foams such as those disclosed in U.S. Pat. Nos. 3,903,232, 4,137,200 and 4,160,076 which are prepared from crosslinked isocyanate-capped polyoxyethylene polyol prepolymer having an average reactive functionality of two or linear isocyanate-capped polyoxyethylene polyol prepolymer having an average reactive functionality greater than two.

Still another surprising characteristic of the polyurethane-poly(N-vinyl lactam) interpolymer foams of this invention lies in their significantly reduced peel adhesion to skin and other tissue as compared to known polyurethane foams. Peel adhesion, a quantitative measurement of adherence of a bandage or dressing to the skin, is the force per unit width necessary to peel the bandage or dressing from a surgical incision or wound site at a constant rate and angle of pull. When, for example, a bandage fabricated from the foam herein is pulled from the site of a partially healed surgical incision, the patient is likely to experience appreciably less discomfort than would be the case with the removal of a bandage manufactured from known types of polyurethane foams. While not wishing to be bound by any explanation for this useful property, it has been speculated that the interpolymerized poly(N-vinyl lactam) is largely responsible for the reduced adhesiveness of the foams of this invention.

DESCRIPTION OF THE PREFERRED EMBODIMENTS

The foams of this invention are prepared from a substantially linear isocyanate-capped polyether polyol prepolymer having a reactive functionality averaging less than about 2.0, e.g., from about 1.3 to about 1.9 and preferably from about 1.5 to about 1.8. A mixture of prepolymers can be used, even one containing one or more prepolymers having a reactive functionality of two and greater, provided the mixture as a whole possesses an average reactive functionality below the prescribed critical upper limit of about 2.0.

The substantially linear polyether polyol component of the prepolymer is derived from a difunctional, active hydrogen-containing initiator, e.g., an aliphatic diol such as ethylene glycol, propylene glycol or 1,4-butanediol and one or more 1,2-epoxides which will impart hydrophilic properties to the resulting polyol, e.g., ethylene oxide or propylene oxide. Polyols of this type are well known and numerous representatives thereof are commercially available. The preferred polyether polyols are derived from ethylene glycol and ethylene oxide and may be represented by the general formula

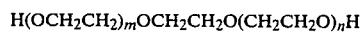

wherein m and n each is an integer of from 2 to about 250, and preferably from about 5 to about 80, and m and n taken together is an integer of from about 3 to about 500 and preferably from about 20 to about 200. In terms of their average molecular weights, these polyols can range from about 200 to about 20,000 and preferably from about 800 to about 10,000.

The selected linear polyether polyol is reacted, or capped, with an amount of a diisocyanate calculated to provide a correspondingly substantially linear prepolymer having an average reactive functionality of less than about 2.0. Suitable diisocyanates include toluene-2, 4-diisocyanate, toluene-2,6-diisocyanate, commercial mixtures of toluene-2,4- and 2,6 diisocyanates, cyclohexylene-1,4-diisocyanate, m-phenylene diisocyanate, 3,3-diphenyl-4,4-biphenylene diisocyanate, 4,4-biphenylene diisocyanate, 1,6-hexamethylene diisocyanate, 1,5-naphthalene diisocyanate, cumene-2,4-diisocyanate, 2,4-diisocyanatodiphenylether, 5,6-dimethyl-1, 3-phenylenediisocyanate, 2,4 dimethyl-1,3-phenylene-diisocyanate, 2,4-dimethyl-1,3-phenylenediisocyanate, 4,4-diisocyanatodiphenylether, 9,10-anthracene diisocyanate, 2,4-diisocyanatotoluene, 1,4-anthracene diisocyanate, 2,4,6-toluene triisocyanate, isophorone diisocyanate and p,p',p",-triphenylmethane triisocyanate. Toluene-2, 4-diisocyanate and diisocyanate mixtures containing toluene-2,4-diisocyanate are especially preferred due to their relatively low cost and ready commercial availability.

The linear isocyanate-capped polyether polyols which are useful in making the polyurethane of this invention are desirably liquid or melt below 100° C. since the foaming operation is generally conducted at temperatures below about 100° C. This consideration is a practical one since the foaming agent employed, i.e., water*, will form steam at temperatures of 100° C. and above presenting safety and handling difficulties with most equipment. Moreover, at temperatures of 100° C. and above, the reaction of prepolymer and water takes place so rapidly that foam formation can be difficult to control. Accordingly, it is preferred that the prepolymer herein be liquid at a temperature which is well below 100° C., e.g., 50° C. and even more preferably, that it be liquid at ambient temperature.

*As those skilled in the art are aware, the actual foaming agent is carbon dioxide gas which is released when the free isocyanate groups of the prepolymer react with water to effect polyurethane formation.

To effect foaming, the prepolymer or prepolymer mixture herein, which may or may not contain one or more other materials, is reacted with a relatively large molar excess of water. The water can be provided as water per se, preferably deionized water, or as an aqueous solution containing one or more of the other components of the foam, e.g., poly(N-vinyl lactam) and/or surface active agent, both of which are readily soluble therein. Where desired, prepolymer and/or aqueous component can contain one or more active ingredients, for example, a drug, bio-affecting or body treating component. However, since the isocyanate groups of the prepolymer are quite reactive, in most cases the active ingredient will be added to the aqueous component, if necessary employing a mutual solvent, emulsifier or dispersing agent if the active ingredient is insoluble in water.

In polyurethane foaming reactions, one mole of water ultimately consumes two isocyanate (NCO) groups. In the present invention, the amount of water employed can range from about 6.5 to about 400 moles, and preferably from about 20 to about 200 moles, per mole of isocyanate groups.

While the foaming reaction can be carried out at about 100° C., for the reasons given above it is generally preferred to conduct this operation at much lower temperatures, e.g., from about 0° C. to 50° C. and better yet, at ambient temperature, if acceptable reaction rates and product characteristics can be achieved. Conventional batch or continuous production equipment is contemplated.

A surface active agent which serves to regulate cell formation during foaming is added to the reaction mixture prior to commencement of foaming, usually as part of the aqueous component. The amounts employed can vary widely with from about 0.5 to about 5.0, and preferably from about 1.0 to about 2.0, percent by weight of prepolymer being suitable for most applications. The use of a surface active agent for this purpose is conventional and widely practiced. In general, any of the surface active agents heretofore used in polyurethane foam manufacture to control cell formation can be effectively used herein. Ethylene oxide-propylene oxide block copolymers (80/20) ratio have been found to provide good results.

The term "poly(N-vinyl lactam)" as used herein shall be understood to include homopolymers and copolymers of such N-vinyl lactams as N-vinylpyrrolidone, N-vinylbutyrolactam, N-vinylcaprolactam, and the like, as well as the foregoing prepared with minor amounts, for example, up to about 20 weight percent, of one or a mixture of other vinyl monomers copolymerizable with the N-vinyl lactams. The amount of poly(N-vinyl lactam) homopolymer/copolymer employed is not critical and advantageously can vary from about 0.5 to 30, and prefereably, from about 5.0 to about 25.0 percent, by weight of prepolymer. Ordinarily, the poly(N-vinyl lactam), being water soluble, will be added to the aqueous component of the reaction mixture prior to commencement of foaming. Of the poly(n-vinyl lactams), the polyvinyl- pyrrolidones homopolymers (PVP) are preferred. A variety of polyvinylpyrrolidones are commercially available from several sources and of these, a polyvinylpyrrolidone having a K-value of at least about 85 is especially preferred.

Advantageously, the foams of this invention will possess a density of from about 1.5 to about 15 lbs. per cubic foot although densities below and above this range can also be used.

As previously indicated, many different types of additives can be incorporated into the polyurethanepoly(N-vinyl lactam) interpolymer foams herein during their manufacture, specifically, during the foaming operation where they will usually be added to the aqueous component of the reaction mixture. Useful additives include organic and inorganic salts, alcohols, amines, acids, polymer latices, resin or wax dispersions, fillers, fibers, cellulosics, surfactants, pigments, dyes, enzymes, proteins, chelates, thickeners, stabilizers, and so forth. The foams of this invention are especially useful as carriers for a wide variety of biologically active substances having curative or therapeutic value for human beings or non-human animals. Included among the biologically active materials which are suitable for incorporation into the foams of the present invention are: hypnotics, sedatives, tranquilizers, anti-convulsants, muscle relaxants, antiparkinson agents, analgesics, antipyretic agents, antiinflammatory agents, local anesthetics, antispasmodics, antiulcer agents, antivirals, antibacterials, antifungals, antimalarials, sympathomimetic agents, cardiovascular agents, diuretics, antiparasitic agents, antitumor agents and hypoglycemic agents, and so forth. By homogenously distributing these materials in the aqueous reaction component, it is possible to effect wide and substantially uniform distribution of these materials throughout the finally prepared foam.

It is also possible to combine the foams herein with a wide variety of substrates including fabrics, either woven or non-woven, paper, other resins, and the like.

The foams of this invention can be positioned upon the surface of the body or inserted in a body cavity such as the vagina (for example, to treat vaginitis) or they can be implanted in body tissue. The foams can be suitably configured for particular applications using conventional techniques, e.g., molding to shape during the foaming operation or cutting the foamed material to the desired configuration.

A particular application for the present foams which fully exploits their advantageous properties is as a carrier for iodine. When immersed in a solution of this agent, the latter will complex with the interpolymerized poly(N-vinyl lactam). Alternatively, before foam formation, the poly(N-vinyl lactam) can be complexed with iodine, the resulting poly(N-vinyl lactam) iodine complex then being dissolved in the aqueous component of the foam-forming reaction mixture. Water soluble complexes of polyvinylpyrrolidone-iodine (povidone-iodine) are known from U.S. Pat. Nos. 2,706,701, 2,826,532 and 2,900,305, the disclosures of which are incorporated by reference herein. The foam can be shaped before or after being combined with iodine into cylinders having concave sides which permit them to be easily fitted between the toes of individuals desiring treatment of athlete's foot (*tinia pedis*). The foam will release its complexed iodine over an extended period of time and so serve to kill fungi (*Trychophyton mentagrophytes*) and bacteria associated with this condition. The high absorptivity of the medicated foam for moisture helps keep the toes dry thus facilitating healing, and the high tensile strength of the foam helps to maintain the physical integrity of the treatment device under thermally and mechanically stressful conditions.

The present foams are also advantageously employed as surgical bandages and wound dressings. The high capacity for absorbing aqueous liquids such as surgical and wound exudates coupled with their low levels of adhesion to surgical or wound sites make the foams herein excellent materials for these and related uses.

COMPARATIVE EXAMPLE

This example illustrates the preparation and aqueous absorptive capacity of a cross-linked polyurethane foam prepared from an isocyanate-capped polyoxyethylene polyol having a reactive functionality greater than two as disclosed in U.S. Pat. No. 4,160,076. The example also reports the aqueous absortive capacity of the foam when interpolymerized with varying amounts of the preferred poly(N-vinyl lactam), polyvinylpyrrolidone.

A prepolymer component consisting of 19.0 g Hypol 2002 (W.R. Grace & Co.) which is prepared by reacting a mixture of polyethylene glycol having an average molecular weight of 1,000 (PEG-1,000) with a trihydroxy alcohol such as trimethylolpropane with a slight molar excess of toluene diisocyanate (TDI) to provide a product having a reactive functionality greater than 2 was reacted with an aqueous component consisting of 26.1 g deionized water containing 2.0 g of a 10% aqueous solution of Pluronic F88 (BASF Wyandotte Corp.), a non-ionic surface active agent which is an 80/20 block copolymer of ethylene oxide/propylene oxide. The prepolymer component and aqueous component were briefly mixed then quickly poured into a mold of desired configuration and the mold was closed. After about 5 minutes, the mold was opened and a thin slab of polyurethane foam was removed. Following washing with water and removal of the excess wash water, the foam, FOAM A, was dried.

Two additional foams, FOAMS B and C, were prepared employing substantially the same procedure as described above except that the aqueous component of the foam-forming reaction mixture for FOAM B contained about 2.4 g of dissolved polyvinylpyrrolidone (GAF Corporation's K-90 grade) and that for FOAM C contained about 4.8 g of the polyvinylpyrrolidone to provide levels of interpolymerized polyvinylpyrrolidone of about 10 and 20 percent by weight of prepolymer, respectively.

Each of FOAMS A,B and C were immersed in two different liquids, one being water, the other saline. The foams were removed from the liquids, non-absorbed liquid was permitted to flow from the suspended foams and the foams were then weighed. The results are set forth in the following table:

TABLE I

| ABSORPTIVE CAPACITY OF CROSSLINKED POLYURETHANE AND CROSSLINKED POLYURETHANE-POLYVINYLPYRROLIDONE INTERPOLYMER FOAMS FOR AQUEOUS LIQUID | | | |
| --- | --- | --- | --- |
| Aqueous Liquid | Foam A (0% PVP) | Foam B (10% PVP) | Foam C (20% PVP) |
| Water | 284 | 679 | 964 |
| Saline | 284 | 566 | 850 |

These data show that the presence of interpolymerized polyvinylpyrrolidone will dramatically increase the absorptive capacity of a known type of crosslinked polyurethane foam for aqueous liquids.

EXAMPLE

This example demonstrates the preparation of substantialy linear polyurethane-polyvinylpyrrolidone interpolymer foams in accordance with this invention. The superior peel adhesion of foams compared to TELFA, a known low-adherence bandage, and the increased aqueous liquid absorptive capacity of the foams compared to a similar foam containing no interpolymerized polyvinylpyrrolidone are given.

A prepolymer component consisting of 19.0 g of Trepol A-15 (Twin Rivers Engineering Co.) which is prepared by reacting 3 weight parts of PEG-1000 with 1 weight part of TDI in a thin film continuous reactor at elevated temperature to provide a product having a reactive functionality of 1.6–1.8 was reacted with an aqueous component consisting of 26.1 g deionized water containing 2.0 g of a 10% aqueous solution of Pluronic F-88. The two components were combined, molded and treated following molding in substantially the same manner described in the Comparative Example to provide FOAM D. Two additional foams, FOAMS E and F containing approximately 10 and 20 weight percent, respectively, of interpolymerized polyvinylpyrrolidone, were also prepared following essentially the same procedure as in the Comparative Example.

Comparision was made between FOAMS D and E and the commercial bandage TELFA for peel adhesion and fluid absorption of exudate. Split thickness defects were made on the backs of surgically prepared rabbits with a Reese Dermatome. After all punctate bleeding had been removed with damp gauze, standard samples (1 in. ×3 in.) of dressing material were placed on the defect and held in place by a dressing and tape. After 24 hours, the samples were exposed and the average force necessary to remove the dressings in a standard manner was measured using a continous drive strain gauge connected to an amplifier and calibrated recorder. The results of the peel adhesion and fluid absorption are set forth in the following table:

TABLE II

PEEL ADHESION AND FLUID ABSORPTION RESULTS

| Test | Telfa | Foam D (0% PVP) | Foam E (10% PVP) |
|---|---|---|---|
| Peel Adhesion (gm/1 in. width) | 13.41 | 4.88 | 3.05 |
| In vivo Fluid Absorption (g/in.$^3$) | 0.65 | 1.28 | 1.65 |

These data show superior performance for both peel adhesion and fluid absorption of a foam prepared in accordance with this invention (FOAM E) over a known type of bandage (TELFA) and a foam containing no interpolymerized polyvinylpyrrolidone (FOAM D). Comparison was also made between FOAMS D,E and F for absorption of water and saline substantially as described in the Comparative Example. The results were as follows:

TABLE II

ABSORPTIVE CAPACITY OF LINEAR POLYURETHANE AND LINEAR POLYURETHANE—POLYVINYLPYRROLIDONE INTERPOLYMER FOAMS FOR AQUEOUS LIQUID
(Wt. % Gain)

| Aqueous Liquid | Foam D (%0 PVP) | Foam E (10% PVP) | Foam F (20% PVP) |
|---|---|---|---|
| Water | 602 | 1061 | 1175 |
| Saline | 534 | 969 | 980 |

These data show substantially greater increases of aqueous liquid absorption for the foams of this invention (FOAMS E and F) compared to the same linear foam containing no interpolymerized polyvinylpyrrolidone (FOAM D) and crosslinked polyurethane foams both with and without interpolymerized polyvinylpyrrolidone (FOAMS A, B and C of the Comparative Example).

What is claimed is:

1. A hydrophilic, flexible, open cell polyurethanepolyvinylpyrrolidone interpolymer foam obtained from the process which comprises reacting under interpolymer and foam-forming conditions (a) a substantially linear isocyanate-capped polyether polyol prepolymer having an average reactive functionality of less than about 2.0 with (b) a poly(N-vinyl lactam) and (c) a foam-forming amount of water in the presence of (d) a cell formation-regulating amount of surface active agent.

2. The foam of claim 1 in which the prepolymer has an average reactive functionality of from about 1.3 to about 1.9.

3. The foam of claim 1 in which the prepolymer has an average reactive functionality of from about 1.5 to about 1.8.

4. The foam of claim 1 in which the prepolymer is prepared with a substantially linear polyether polyol derived from a difunctional, active hydrogen-containing initiator and one or more 1,2-epoxides which will impart hydrophilic properties to the resulting polyol.

5. The foam of claim 1 in which the prepolymer is prepared with a substantially linear polyether polyol derived from ethylene glycol and ethylene oxide.

6. The foam of claim 1 in which the prepolymer is prepared with a substantially linear polyether polyol of the general formula $H(OCH_2CH_2)_mOCH_2CH_2O(CH_2CH_2O)_nH$ wherein m and n each is an integer of from 2 to about 250 and m and n taken together is an integer of from about 3 to about 500.

7. The foam of claim 6 in which m and n is an integer of from about 5 to about 80 and m and n taken together is an integer of from about 20 to about 200.

8. The foam of claim 6 in which the average molecular weight of the polyol is from about 200 to about 20,000.

9. The foam of claim 6 in which the average molecular weight of the polyol is from about 800 to about 10,000.

10. The foam of claim 1 in which the prepolymer is prepared with a toluene diisocyanate.

11. The foam of claim 1 in which from about 6.5 to about 400 moles of water are reacted with the prepolymer.

12. The foam of claim 1 in which from about 20 to about 200 moles of water are reacted with the prepolymer.

13. The foam of claim 1 in which the poly(N-vinyl lactam) is a polyvinylpyrrolidone.

14. The foam of claim 1 in which the poly(N-vinyl lactam) is a polyvinylpyrrolidone having a K-value of about 85.

15. The foam of claim 1 in which the surface active agent is a non-ionic surface active agent.

16. The foam of claim 1 prepared with from about 0.5 to about 5.0 percent surface active agent by weight of prepolymer.

17. The foam of claim 1 prepared with from about 1.0 to about 2.0 percent surface active agent by weight of prepolymer.

18. The foam of claim 1 containing a drug, bio-effecting or body treating ingredient.

19. The foam of claim 1 containing bioavailable iodine complexed with the interpolymerized poly(N-vinyllactam).

20. The foam of claim 13 containing bioavailable iodine complexed with the interpolymerized polyvinylpyrrolidone.

21. An athlete's foot treatment article prepared with the foam of claim 1.

22. An athlete's foot treatment articles prepared with the foam of claim 19.

23. An athlete's foot treatment article prepared with the foam of claim 20.

24. A surgical dressing or bandage prepared with the foam of claim 1.

25. A vaginitis treatment articles prepared with the foam of claim 1.

* * * * *